US006582931B1

United States Patent
Kois et al.

(10) Patent No.: US 6,582,931 B1
(45) Date of Patent: Jun. 24, 2003

(54) DENTO-FACIAL ANALYZER

(75) Inventors: John C. Kois, Federal Way, WA (US); Thomas E. Lee, Brand Terrace, CA (US)

(73) Assignee: Panadent Corporation, Grand Terrace, CA (US)

( * ) Notice: Subject to any disclaimer, the term of this patent is extended or adjusted under 35 U.S.C. 154(b) by 94 days.

(21) Appl. No.: 09/722,478

(22) Filed: Nov. 8, 2000

(51) Int. Cl.[7] .......................... A61C 11/00; A61C 19/04
(52) U.S. Cl. .............................. 435/56; 433/55; 433/63; 433/68; 433/71; 433/73; 33/513
(58) Field of Search .................. 433/54, 55 R, 433/56 OR, 57, 58, 59, 60, 61, 62, 63 R, 64, 65, 66, 67, 68 R, 71 R, 73 R; 33/513, 514

(56) References Cited

U.S. PATENT DOCUMENTS

| | | | | |
|---|---|---|---|---|
| 1,589,973 A | * | 6/1926 | Landa .......................... | 33/514 |
| 2,548,817 A | * | 4/1951 | Raiche ......................... | 433/71 |
| 2,613,440 A | * | 10/1952 | Murray et al. ................. | 433/56 |
| 2,648,130 A | * | 8/1953 | Avery .......................... | 433/73 |
| 2,731,723 A | * | 1/1956 | Brandhandler ............... | 433/60 |
| 2,748,481 A | * | 6/1956 | Glueck ........................ | 433/55 |
| 3,200,497 A | * | 8/1965 | Goodfriend ................... | 433/44 |
| 3,693,260 A | * | 9/1972 | Hernandez .................... | 433/56 |
| 3,854,208 A | * | 12/1974 | Arant ........................... | 433/73 |
| 4,624,639 A | * | 11/1986 | Wong .......................... | 433/56 |
| 5,176,515 A | * | 1/1993 | Andrews ...................... | 433/24 |
| 5,971,756 A | * | 10/1999 | Fjelstad ....................... | 433/68 |

OTHER PUBLICATIONS

Precision Instrument Systems for Occlusal Treatment and Diagnosis, DENAR/HANAU, Teledyne Water Pik, 1998, front and back cover and p. 36.

* cited by examiner

Primary Examiner—John J. Wilson
(74) Attorney, Agent, or Firm—Knobbe, Martens, Olson & Bear, LLP

(57) ABSTRACT

A face bow assembly including a face bow having a bite fork portion to carry an index trays to be positioned in a patient's mouth. The bow has outwardly extending wings to enable a dentist to support the bow. A vertical indicator rod mounted to the bow helps align the tray horizontally and the indicator rod vertically to the patient's mid-sagittal, while bite impression material on the tray hardens. The upper index tray is then mounted on a platform on a dental articulator. The platform has an incisal line for alignment with an incisal line(s) for adjustability on the upper index tray. The platform also has vertical or horizontal adjustability with a built-in scale.

53 Claims, 9 Drawing Sheets

DENTO-FACIAL ANALYZER

FIELD OF THE INVENTION

The present invention relates to dental apparatus, and more particularly to a simplified system for transferring dental-facial information from a patient to a dental articulator to facilitate accurate mounting of dental study casts on the articulator for the diagnosis and treatment of both aesthetics and function.

BACKGROUND OF THE INVENTION

In analyzing and treating jaw disorders and in making dental prostheses, it is desirable to simulate the patient's jaw movements. To do this on a dental articulator, it is first necessary to analyze the jaw movements and then transfer the information to a dental articulator to enable the articulator to move in a manner to simulate the patient's jaw movements. This enables the dentist or technician to test and shape dental prostheses on the articulator before mounting them in the patient's mouth.

In one system for analyzing jaw movements, an upper frame or face bow is mounted on a patient's nose and ears with side arms supporting rigid recording plates overlying the patient's temporomandibular joints. A grid of intersecting lines on graph paper is provided on the recording plates. A lower or mandibular frame is mounted by means of a dental clutch to the patient's lower jaw so as to move with the jaw with side arms of the lower frame carry writing elements for tracing jaw movements on the graphs.

In use of such apparatus, it is usually initially necessary to locate the hinge axis about which the lower jaw rotates when it is in its rearward most position, and moved in mouth closing and opening directions. Once the hinge axis is located, the jaws are moved in various fashions to provide tracings with respect to a reference line through the hinge axis and a point on the patient's nose or face. The data obtained from the tracings is then used to set a dental articulator.

There are a variety of other systems explained in the literature for obtaining information about the jaw movements, all of which have various complexities and disadvantages.

In mounting dental casts to an articulator, it is necessary to position the cast in the same relation to each other as the teeth in the patient's mouth as well as being orientated or related to the patient's hinge axis. In accomplishing that, impressions of the patient's bite are made in impression material positioned on a flat bite fork which is clamped between the patient's upper and lower teeth. The position of the bite fork in relation to a reference plane on the patient is determined using an arbitrary axis face bow also known as an ear-bow, and the bite fork is then mounted on the lower frame of the dental articulator in a position to receive the upper dental cast of the patient's teeth. These so-called different reference planes has been referred to as "Frankfort-horizontal," "axis-orbital," or "axis-horizontal" plane of reference. The arbitrary face bow is related to an average distance from the axis of the lower jaw to the ear hole (auditory meatus) to a third point of reference located somewhere on the patient's face. While the cast is held in that position, it is secured by dental plaster to a mounting plate attached to the upper frame of the dental articulator. Once the upper cast is mounted, the lower cast can be secured to the articulator by utilizing the upper cast as a guide along with an interocclusal record.

While these known systems are relatively accurate, they are unfortunately still somewhat complicated and time consuming, requiring many different steps, comprising many components including screws to tighten and bite forks that need to be sterilized before each use. These systems are also related to an average axis-to-earhole distance. As a result, many practitioners do not use a dental articulator but instead employ old manual techniques, and trial and error, or allow technicians to mount into small disposable dental articulators without regard or relation to the hinge axis or lateral movements, in terms of providing proper function and fitting of prostheses on the patient. It is believed that many more practitioners would utilize a dental articulator if the procedures for obtaining patient dental-facial information and mounting that information in a dental articulator were greatly simplified.

In providing dental prostheses, it is only in recent years that more attention is being paid to improving the aesthetic aspects of a patient's teeth at the same time that the functional aspects are being performed or improved. Thus, it is desirable that not only a simplified system for increasing the use of dental articulators, but it is also desirable that the aesthetic aspects be properly addressed.

SUMMARY OF THE INVENTION

Briefly stated, the invention is directed to a system, including apparatus and method, for orienting a patient's bite, capturing or registering in bite registration material the tilt or slant of the occlusal plane of the patient's teeth in three planes of space in relation to the cranium or head and related to an average or specific axis-incisal distance. The registration material is on an index tray positioned on a horizontal face bow analyzer. The invention further includes an adjustable mounting platform on the lower frame of a dental articulator adapted to receive the index tray from the analyzer bow to mount study casts on a dental articulator.

If a patient specific axis-incisal distance is to be used, the operator measures the distance from the patient's approximate hinge axis to the maxillary incisors. The patient's bite is then formed in the registration material on the index tray aligned with marking, such as a line, indicating the forward edge of the patient's incisors. The distance between the line marked on the index tray on the mounting platform and the hinge axis defined in the dental articulator is related to the distance between the patient's incisal edge and the patient's jaw hinge axis. The distance between the articulator hinge axis and the incisal line marked on the index tray on the mounting platform is equal to the average 100 mm corresponding distance for patients. More preferably, the patient's specific axis incisal distance measured previously is marked on the index tray from the average 100 mm line. Or, the mounting platform can be adjustable in an anterior posterior position, that will correlate more closely with measured data obtained from the patient. Further, the platform is preferably vertically adjustable so as to position the selected incisal line at a consistent horizontal distance with respect to the hinge axis and to center the study casts in the articulator.

The face bow analyzer includes a bite fork portion and a pair of gripping wings or handles flaring outwardly from a central portion, protruding forwardly from the bite fork, and wrapping around the patient's face. The forward portion is formed with an elongated slot for receiving a vertical indicator rod. The rod is supported in a holder that is slidably mounted in the slot to enable the rod to be moved close to the patient's face. Preferably, the analyzer face bow is a one-piece thin flat rigid element.

In use, an average value of 100 mm can be used, or preferably, the operator can measure the patient's axis-to-incisal distance and mark the distance measured from the average 100 mm incisal line marked on the index tray. The upper and lower index trays are clamped to the bite fork on the analyzer bow and bite registration material is applied on the trays. The operator then grips the wings on the analyzer bow and inserts the bite fork into the patient's mouth and aligns the maxillary central incisors to the incisal line marked on the upper index tray, while the patient is sitting erect looking straight forward. The indicator rod is then moved rearwardly towards the face, and the dentist adjusts the face bow so that the indicator rod appears vertical and aligned with the patient's midsagittal when viewed from the front. The patient is lightly gripping the impression material on the trays, but the trays are still movable within the impression compound. The operator then views the analyzer bow from the side to get a profile view, and manipulates the bow so that the indicator rod is vertical from that perspective. A level gauge can be added to the analyzer bow to verify the horizontal relation of the bow. The analyzer bow is then horizontally oriented, capturing the patient's tilt or slant of the occlusal plane in relation to the patient's cranium in three planes of space related to an average or specific axis-incisal distance. With the analyzer bow so positioned, the bite registration material is allowed to set or harden.

Once the material has set, the operator can position the O-rings on the vertical indicator rod to different facial landmarks, such as eyes, nose and chin for diagnosing the patient's facial proportions. The height of the right and left lip commisures can also be measured from the index tray and noted in the patient's chart for future reference to be transferred to the study casts on the articulator.

Following that, the operator, gripping the wings on the bow, carefully removes the bite fork from the patient's mouth, and the upper index tray is removed and sent to the laboratory for positioning on the mounting platform supported on the dental articulator to mount the patient's upper cast to the upper frame of a dental articulator. This is done by attaching an adjustable mounting platform, configured to receive upper index tray, to an articulator with the hinge axis related to an incisal line on the index tray. The mounting platform is vertically adjustable with a millimeter scale, that can be set to a desired incisor length.

DETAILED DESCRIPTION OF THE PREFERRED EMBODIMENT

Figure 1:
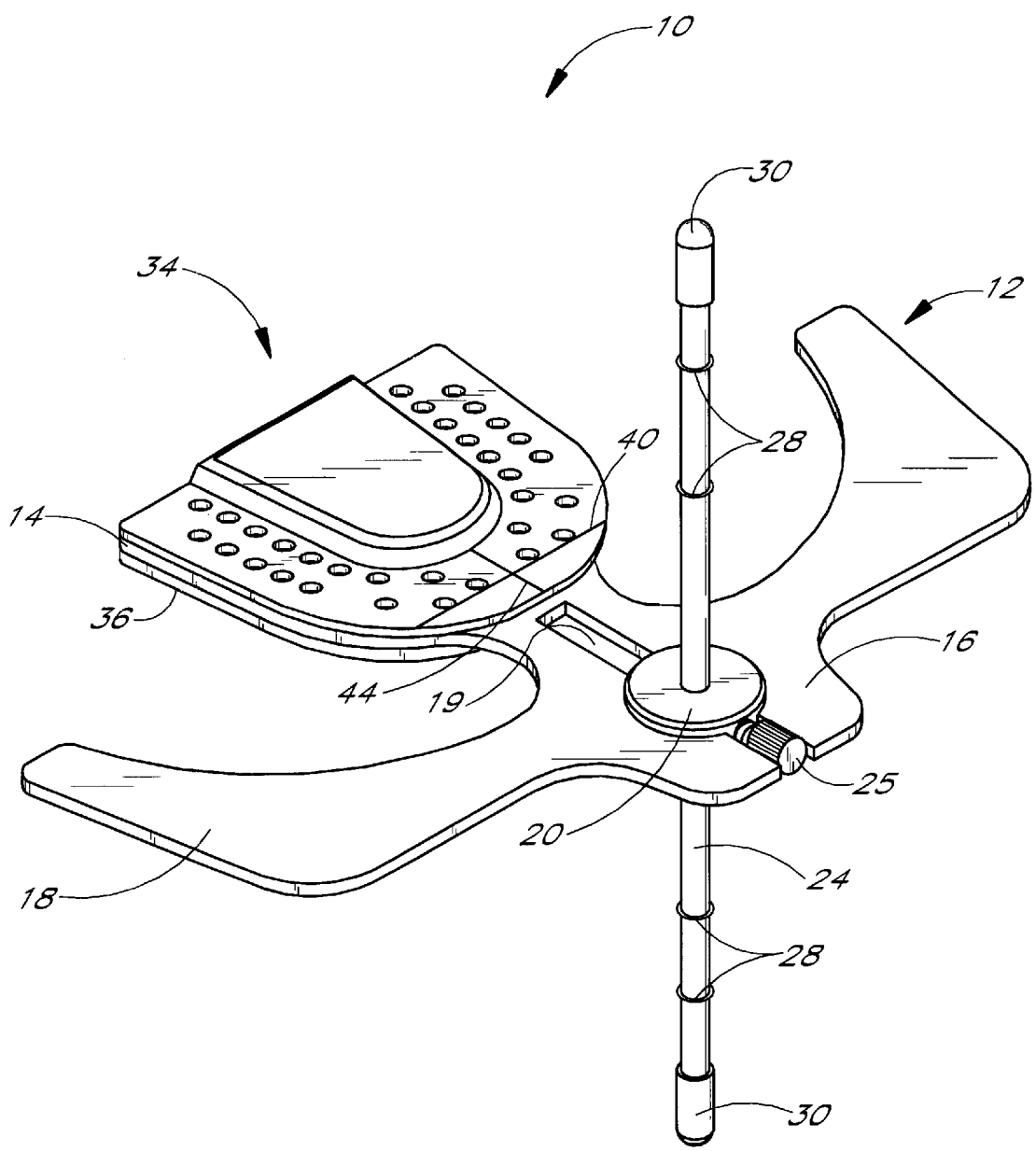
FIG. 1 is a perspective view of an analyzer face bow assembly of the invention.
Figure 2:
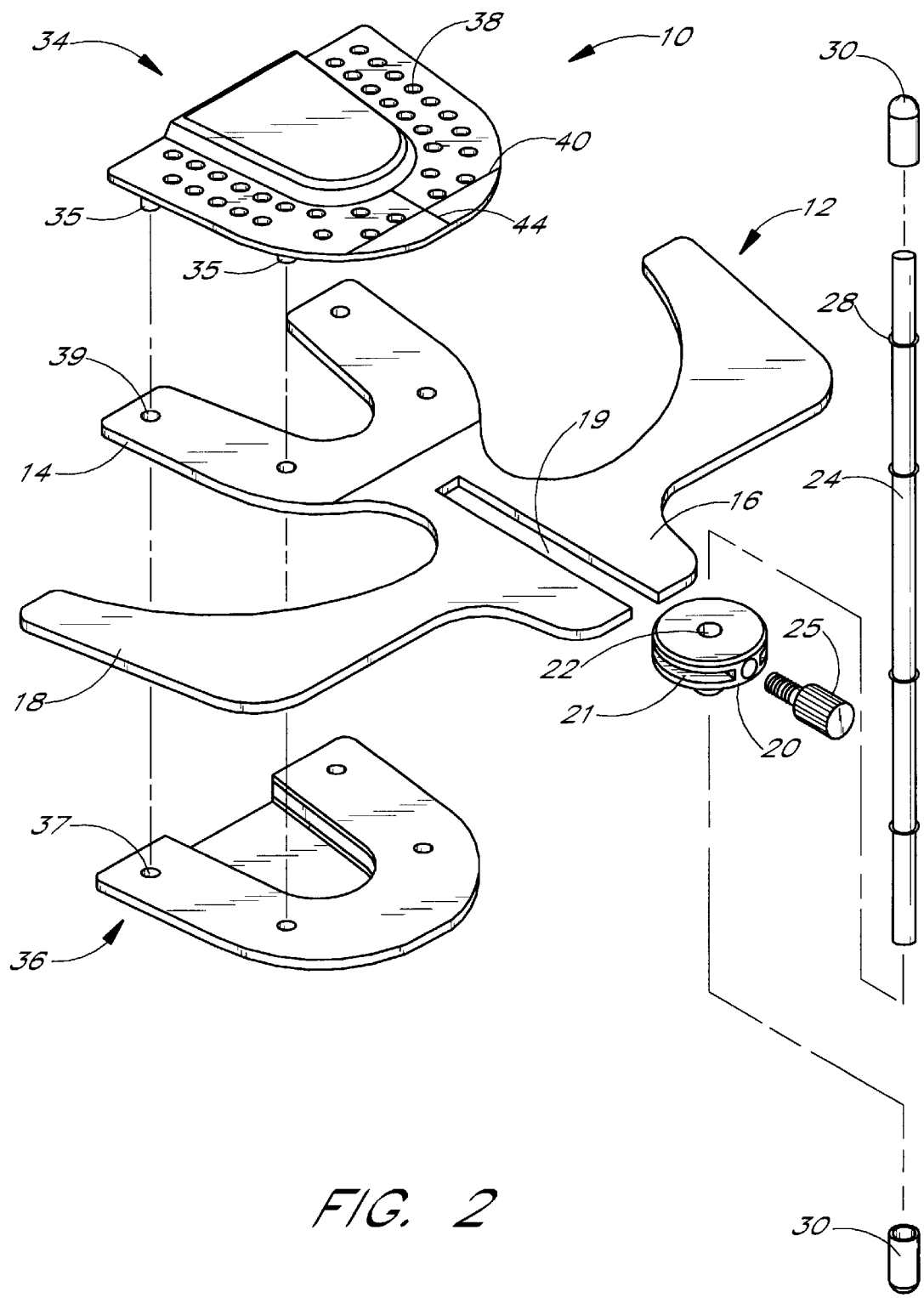
FIG. 2 is an exploded perspective view of the assembly of FIG. 1.

Referring to FIGS. 1 and 2, there is illustrated an analyzer face bow assembly 10, the primary component of which is a face bow 12. The face bow is a multi-function element preferably having a thin flat configuration made of rigid material such as a suitable metal or plastic. It includes a generally U-shaped bite fork or plate 14 sized to mate with a patient's teeth or gums when the jaws are clamped on the plate. The closed forward end of the bite fork leads to a central forward portion 16, and a pair of wings 18 which extend laterally outwardly from the portion 16. The wings are spaced from the bite fork inasmuch as the bite fork 14 is adapted to fit within the patient's mouth and the wings 18 are intended to surround the forward portion of a person's face spaced from the face. The wings 18 could be referred to as handles since they are gripped by the operator when the bow 12 is being installed, adjusted and removed. The central portion 16 includes an elongated straight slot 19 that extends forwardly from the center of the bite fork 14 and opens to the front edge or forward portion 16 of the face bow 12.

A disk-shaped holder 20, which includes grooves 21 on its sides is sized to slide within the slot 19. The holder is formed with a central hole 22 sized to receive a vertical indicator rod 24. This positions the rod 24 perpendicular to the flat bow 12. One or more tubular markers 28 slides on the upper and the lower end of the rod. A protective cap 30 is placed on both ends of the rod 24 for safety. A thumb screw 25 fixes the rod relative to the holder 20.

Figure 3:
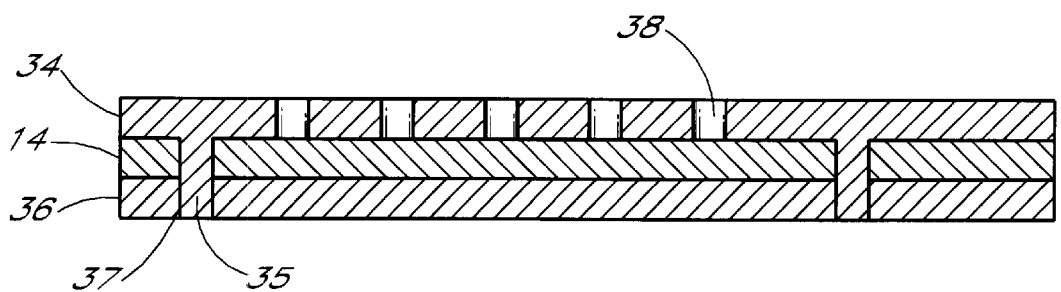
FIG. 3 is cross-sectional view of the index trays positioned on the bite fork portion of the assembly of FIGS. 1 and 2.

The assembly 10 also includes an upper index tray 34 and a lower index tray 36. The upper index tray includes four downwardly extending pins or projections 35 sized to fit within four mating holes 39 formed in the bite fork 14, as seen in FIG. 3. The projections 35 are long enough such that they protrude through the bite fork 14 and fit within four mating holes 37 in the lower index tray 36.

The upper index tray 34 and lower index tray 36 are also provided, with a number of small holes 38 for receiving bite registration material such as impression compound. If desired, the holes 38 can be made frusto-conical in shape, having a smaller diameter at its upper end and a larger diameter at its lower end with tapered sides in-between to help capture impression material. The upper surface of the upper tray has a marking 40 referred to as an incisal line, and has a central line 44 which is perpendicular to and bisects the incisal line 40.

Figure 4:
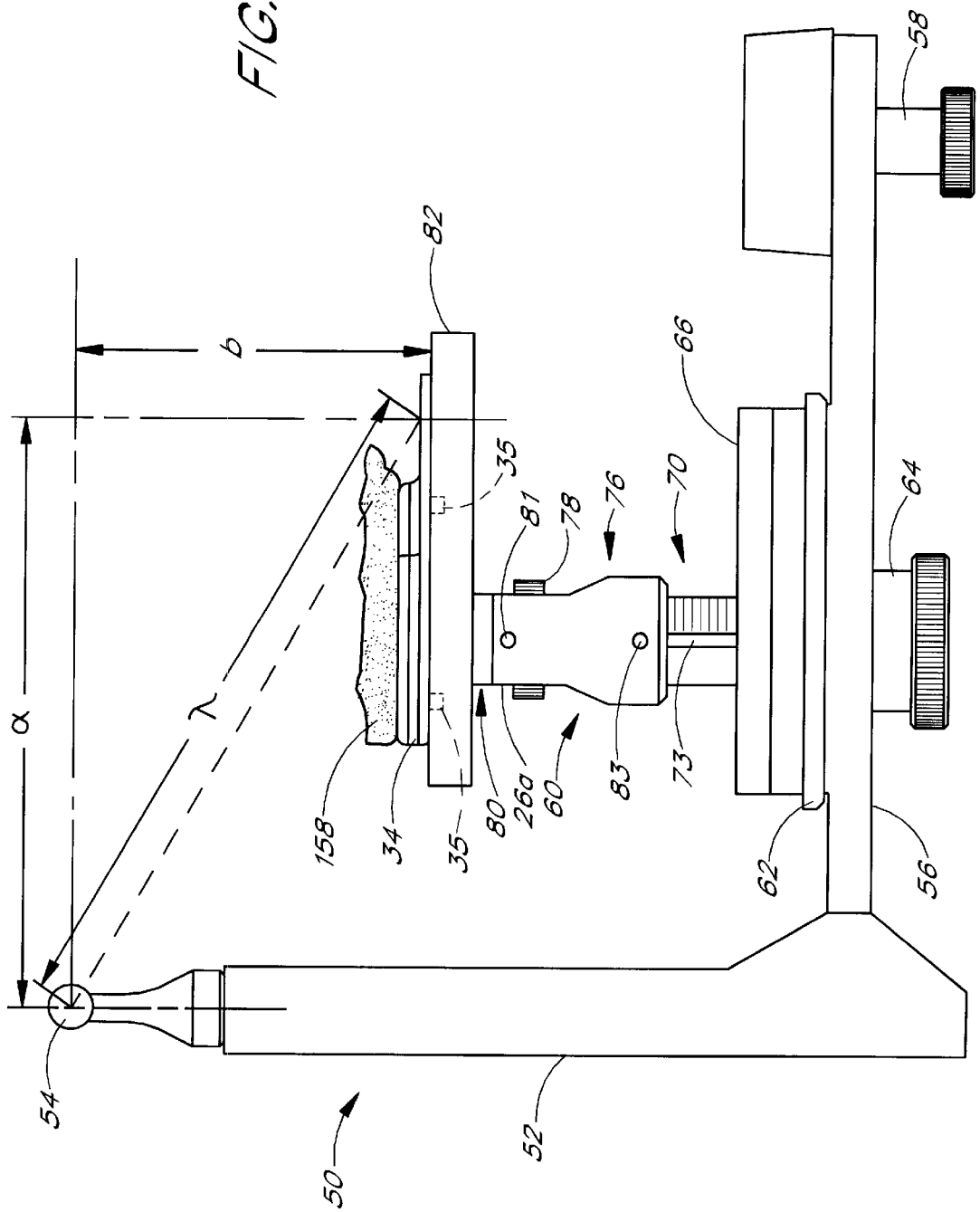
FIG. 4 is a side elevational view of the lower frame of a dental articulator illustrating an upper index tray from FIGS. 1 and 2 mounted on a platform assembly supported on the articulator frame.

FIG. 4 illustrates the lower frame 50 of a dental articulator, which includes a vertical frame member 52 topped by a pair of balls 54, one of which is shown in FIG. 4. The ball centers define a hinge axis. A horizontal lower frame member 56 is connected to the lower portion of the vertical member 52 and is supported on its forward end by a leg 58. A mounting platform assembly 60 is mounted on a magnetic base plate 62 secured to the lower frame member 56 by a fastener 64.

Figure 5:
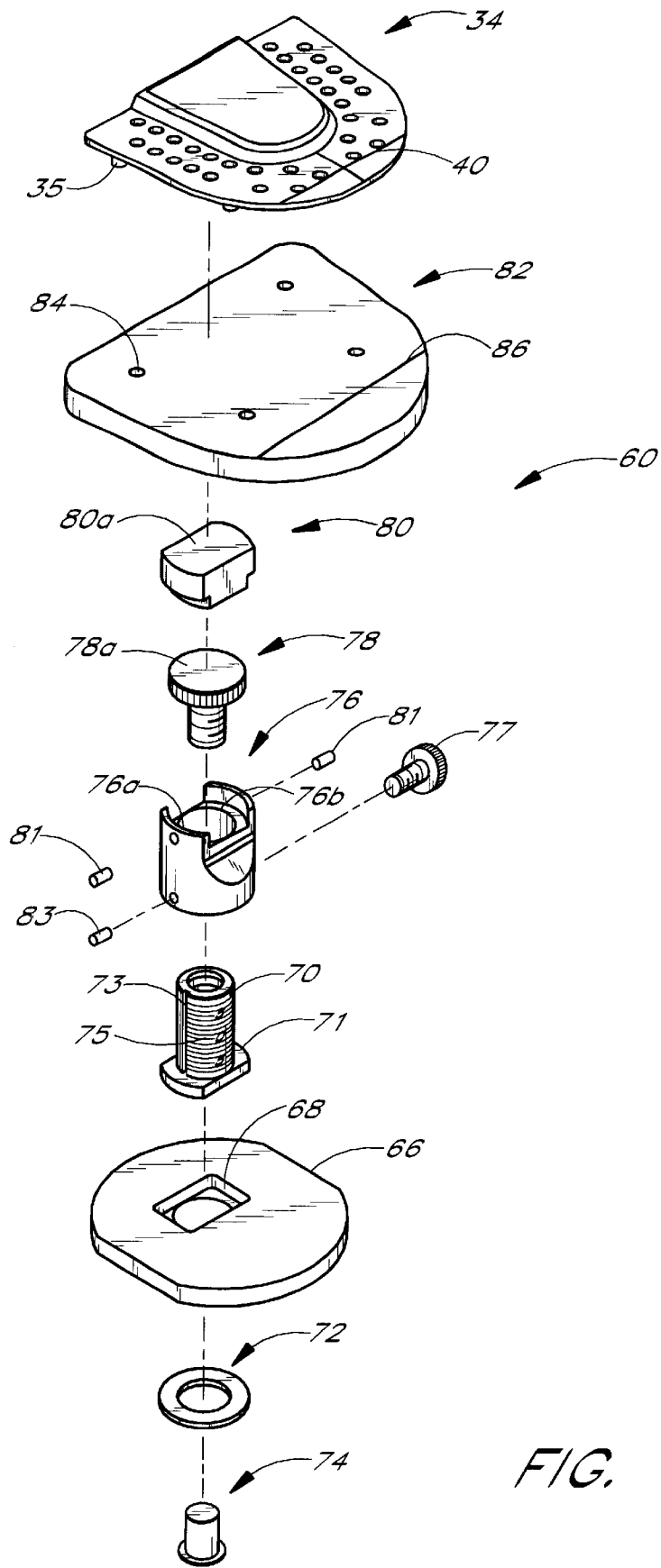
FIG. 5 is an exploded perspective view of the components of the mounting platform of FIG. 4 and the upper index tray of FIG. 2.

Referring to FIGS. 4 and 5, the mounting platform assembly 60 includes a lower base plate 66 having a generally rectangular recess 68 in its upper surface. A tubular support column 70 formed with a generally rectangular base 71 fits within the recess 68 and prevents the column from rotating. The column 70 is locked to the plate 66 by means of a ferrous metal washer 72 and fastener 74 which extends through a hole in the base plate 66 and threads into the interior of the support column 70. The fastener 74 and the washer 72 adhere to the magnetic mounting plate 62 and fit within a recess in the lower surface of the base plate 66. A support collar 76 adjustably slides onto the upper end of the column 70 and is supported by an adjustment screw 78 threaded into the upper end of the column 70. The head 78a of the adjustment screw 78 fits into a recess 76a in the upper end of the collar 76 and engages a shoulder 76b in the recess. The screw head is captured in the collar 76 recess by the lower end of a connector 80 that fits within the recess 76a and is attached to the collar 76 with dowel pins 81. A generally rectangular head 80a on the connector 80 forms an interference fit within a mating recess in the bottom surface of a mounting platform 82.

Thus, rotating the adjustment screw 78 raises or lowers the platform 82. A pin 83 mounted in the collar 76 extends into an axially extending groove 73 in the exterior of the column 70 to prevent rotation of the collar 76. The exterior of the column has a scale or markings 75 to indicate the vertical adjustment. A locking thumb screw 77 further locks the collar 76 to the column 70 after the vertical adjustment is made.

The platform is positioned in a known relationship with respect to the hinge axis, through the balls 54 which correspond to a patient's hinge axis, and the incisal edge. For proper mounting with the upper index tray 34, the platform 82 preferably has four spaced holes 84 that align with the four projections 35 extending downwardly from the upper index tray 34. The mounting platform 82 preferably has an incisal line 86 marked thereon for alignment with the index tray incisal line 40. However, if only an average incisal line-to-hinge axis distance of 100 mm is used, the line on the platform is not needed. The lines 40 on the upper index tray 34 and line 86 on the platform 82 may of course be marked in any fashion, such as grooves, solid or dashed lines, etc.

Figure 6A:
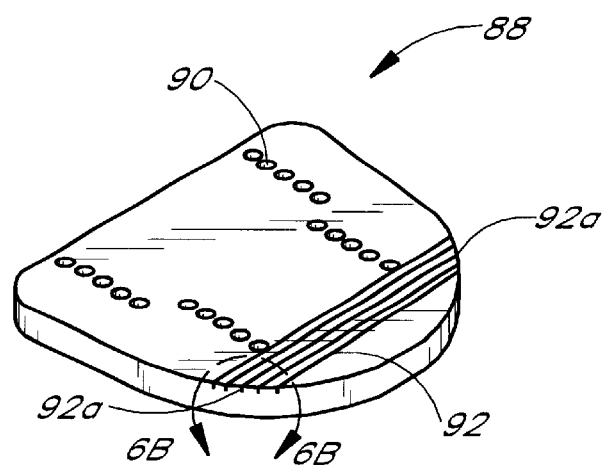
FIG. 6A is a perspective view of an alternate mounting platform of FIG. 5.
Figure 6B:
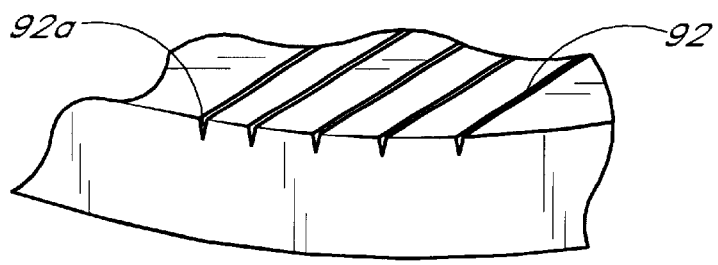
FIG. 6B is an enlarged view of the portion 6B—6B in FIG. 6A.

FIG. 6A illustrates an alternate mounting platform 88. It has five sets of four holes 90 and five spaced incisal lines 92. This enables the index tray 34 to be mounted to the mounting platform 88 in five different positions, such as 90 mm, 95 mm, 100 mm, 105 mm, 110 mm, from a patient hinge axis, such as an incisal line 92. Note also that instead of or in addition to, the outer edges of the lines 92 of the platform 82 and line 40 on the upper iridex tray 34 can be grooved or notched as shown at 92a to mark the edges of the line as seen in FIG. 6B.

Figure 7:
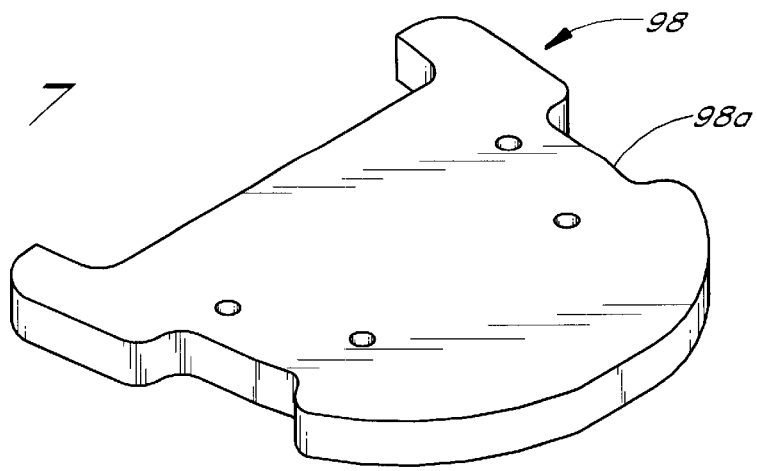
FIG. 7 is a perspective view of another alternate mounting platform of FIG. 5.

FIG. 7 illustrates another form of a mounting plate 98 wherein the sides of the plate are recessed at 98a to facilitate separating an index tray from the plate.

Figure 8:
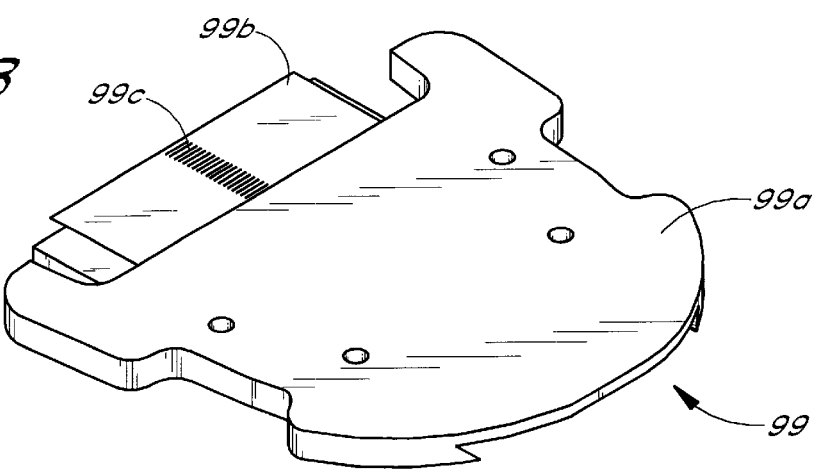
FIG. 8 is a perspective view of a horizontally adjustable platform.
Figure 9:
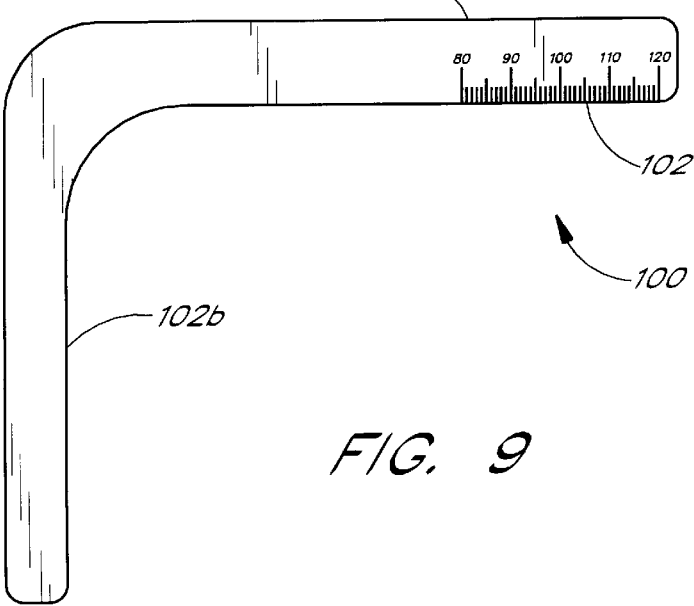
FIG. 9 is a plan view of a tool used to measure a hinge axis-maxillary incisal line distance.

FIG. 8 illustrates an alternate form of a mounting plate 99 that can be horizontally adjusted instead of or in addition to being vertically adjustable. An upper portion 99a is slidably mounted on a lower portion 99b, which can be fixed to the connector 80, shown in FIG. 5. Scale lines 99c indicate the position of the upper portion 99a with respect to the lower portion 99b. A lock screw or other means (not shown) may be provided to lock the two portions together after adjustment.

Operation

Before starting, if a specific axis-incisal distance is to be used, the operator can move the patient's jaw about the temporomandibular joints to locate the approximate hinge axis of the mandible. The operator can measure the distance from this located patient's hinge axis to the patient's maxillary incisal edge and record that distance on the patient's chart, for use in connection with the index tray or in connection with the adjustable mounting platform. If a specific axis-incisal distance is to be used, the operator can measure either forward or backward from the average 100 mm incisal line marked on the upper index tray, and mark the index tray with a new specific axis-incisal line that corresponds with the actual distance measured on the patient.

A patient's incisal distance may be measured by a suitable tool 100 such as that shown in FIG. 8. As seen, the tool has a 90° flat shape, with one arm 100a having distance or scale markings 102 marked thereon. In use, the inner edge of the unmarked arm 102b is placed against the lower edge of the patient's incisors and the arm 100a is placed so that the markings are adjacent the patient's hinge axis. The distance from the incisal line to the axis can then be observed and recorded.

In use, the vertical indicator rod 24 is connected to the analyzer bow 12 by sliding the rod holder 20 into the slot 19 on the bow. Next, an upper index tray 34 is mounted to the bite fork portion 14 of the analyzer bow 12 with its depending or protruding pins 35 extending into the mating holes 39 on the bite fork portion 14. Those pins extend through the bite fork plate and extend into corresponding holes 37 in the lower index tray 36. Thus, the two index trays 34, and 36 are sandwiched or firmly secured to the bite fork portion 14 of the analyzer bow 12. Soft bite registration material, that is, an impression compound or other suitable material, is placed on both the upper and lower occlusal surfaces of the index trays 34 and 36. Care should be taken not to cover the incisal line on the index tray that will be used with the bite registration material.

Before positioning the analyzer bow with respect to the patient, the patient should sit erect on a backless stool and look straight ahead. Preferably, the patient is looking into a mirror, to make it easier for the patient to maintain that desired position. The analyzer bow assembly 10 is then to be mounted to the patient by positioning the bite fork portion 14 into the patient's mouth. The patient's incisal edge of the maxillary incisors should be aligned with the incisal line marked on the upper surface of the index tray. The patient should be instructed to bite lightly into the compound to register impressions of the patient's teeth and to help the operator support the analyzer bow.

Figure 10:
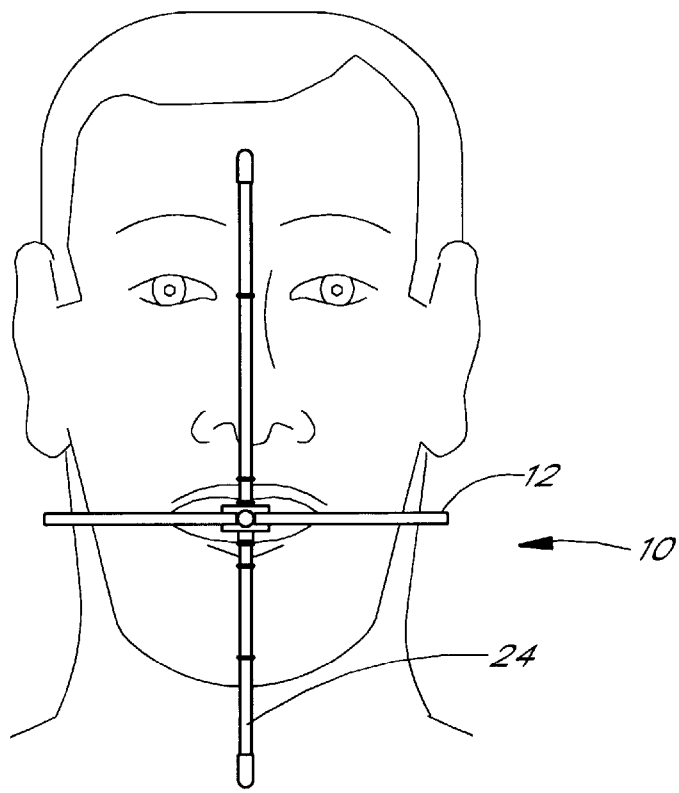
FIG. 10 is a schematic view illustrating the positioning of the face bow of FIG. 1 on a patient from the frontal view.

The vertical indicator rod 24 is then slid rearwardly close to the patient's face within slot 19 of the analyzer bow 12. The analyzer bow assembly 10 is adjusted so that the vertical indicator rod 24, when viewed from the front is aligned with the central mid-sagittal plane through the patient's head, as in FIG. 10. This is done by the operator gripping the wings 18 of the analyzer bow 12 and moving the bow as necessary relative to the patient's teeth and face. That is, the patient is still sitting erect and the bite registration material is still soft such that the index trays mounted on the analyzer bow can be adjusted to make the indicator rod be vertical and centered or aligned to the patient's mid-sagittal when viewed from the front of the patient.

Figure 11:
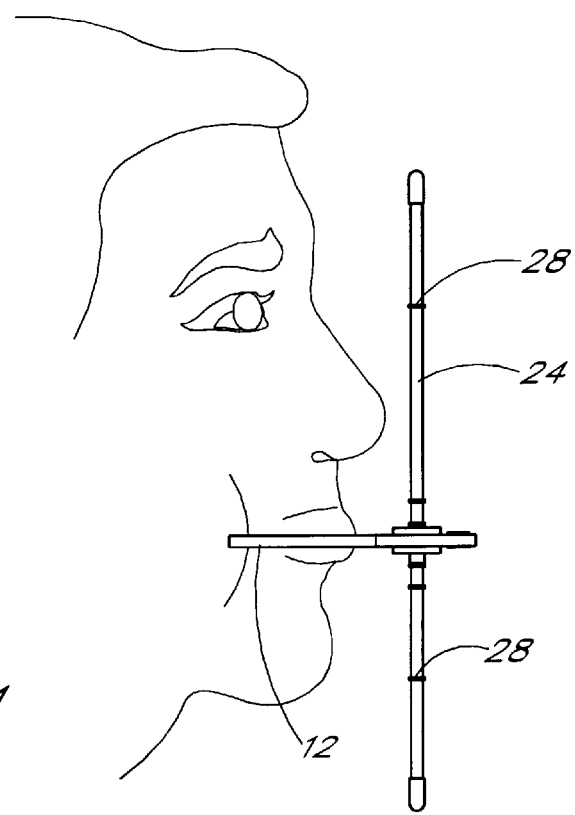
FIG. 11 is a schematic view illustrating the positioning of the face bow of FIG. 1 on a patient from a profile view.

The bow is then viewed from the side, as in FIG. 11, so as to get a profile view, and the bow is adjusted so that it appears horizontal and the rod is vertical. If desired, levels can be added to or incorporated into the wings of the bow to verify or facilitate the leveling action. The analyzer bow is then held in this desired orientation as the bite registration material hardens. The bow now horizontal and the indicator rod now vertical are aligned with respect to the patient's cranium in all three planes of space related to an average 100 mm or specific axis to incisal edge distance.

While the analyzer bow assembly 10 is still mounted to the patient, the patient should be instructed to smile to enable the operator to measure the height of the lip commisures from the upper surface of the upper index tray 34 of the analyzer bow, that is, the distance that the corners of the smile rise above the index tray attached to the analyzer bow. This measurement should be recorded and transferred to the dental cast when mounted in a dental articulator. The height of the eyes, nasal-labial point, incisal edge, the chin, and other specific facial landmarks can also be marked on the vertical indicator rod to evaluate facial proportions. The slidable collars or O-rings 28 can also be used to mark these facial landmarks on the vertical indicator rod.

The patient's mouth can then be opened to permit the operator to carefully remove the analyzer bow assembly 10. The lower index tray 36 can then be removed from the bite fork and discarded. The upper index tray 34 is also removed and sent to the laboratory to be used with the mounting platform as assistance in mounting a dental cast to the dental articulator.

Figure 12:
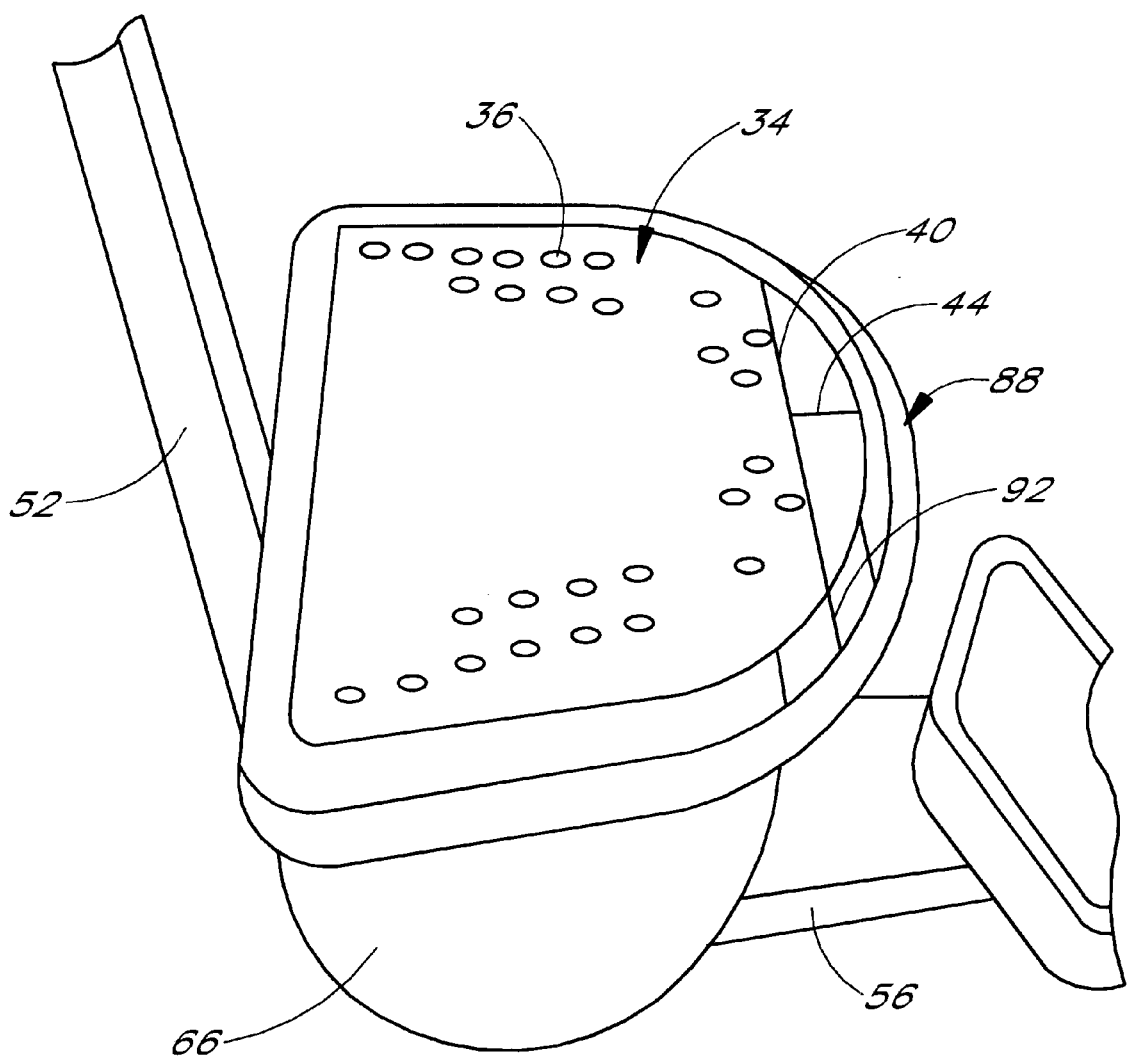
FIG. 12 is a schematic view illustrating the alignment of the upper index tray on the mounting platform attached to the lower frame of a dental articulator.

The adjustable mounting platform assembly 60 is mounted on the lower frame 50 of the dental articulator. The vertical height of the platform 82 is adjusted as desired with the adjustment screw 78 and locked in place with the lock screw 77. If the patient's specific axis-incisal distance was marked on the upper tray and is used, or an average value of 100 mm is used for the distance between hinge axis through the condyle balls 54 on the articulator and the incisal line on the mounting platform, the platform 82 with the single incisal line 86 can be employed, since there would be no adjustment. However, an adjustable mounting platform 88 shown in FIG. 6 could be utilized to orient the index tray in the dental articulator, that best corresponds to the distance from the patient's hinge axis to the maxillary incisal edge. An average value for the distance λ from the hinge axis to the incisal line on a patient is about 100 mm, and that is the dimension used on the upper index tray and on the articulator. The horizontal distance α from the hinge axis to the incisal line on the platform 82 is preferably about 87 mm. The height of the platform above the articulator frame member 56 is preferably centered between the upper and lower frames of the articulator. In a preferred arrangement, the height β is about 60 mm. This equal spacing between the frames of the articulator and the dental casts allows room for magnetic mounting plate systems, index systems, dental implants and other procedures. FIG. 12 illustrates the tray properly mounted on the platform (without the impression material).

Figure 13:
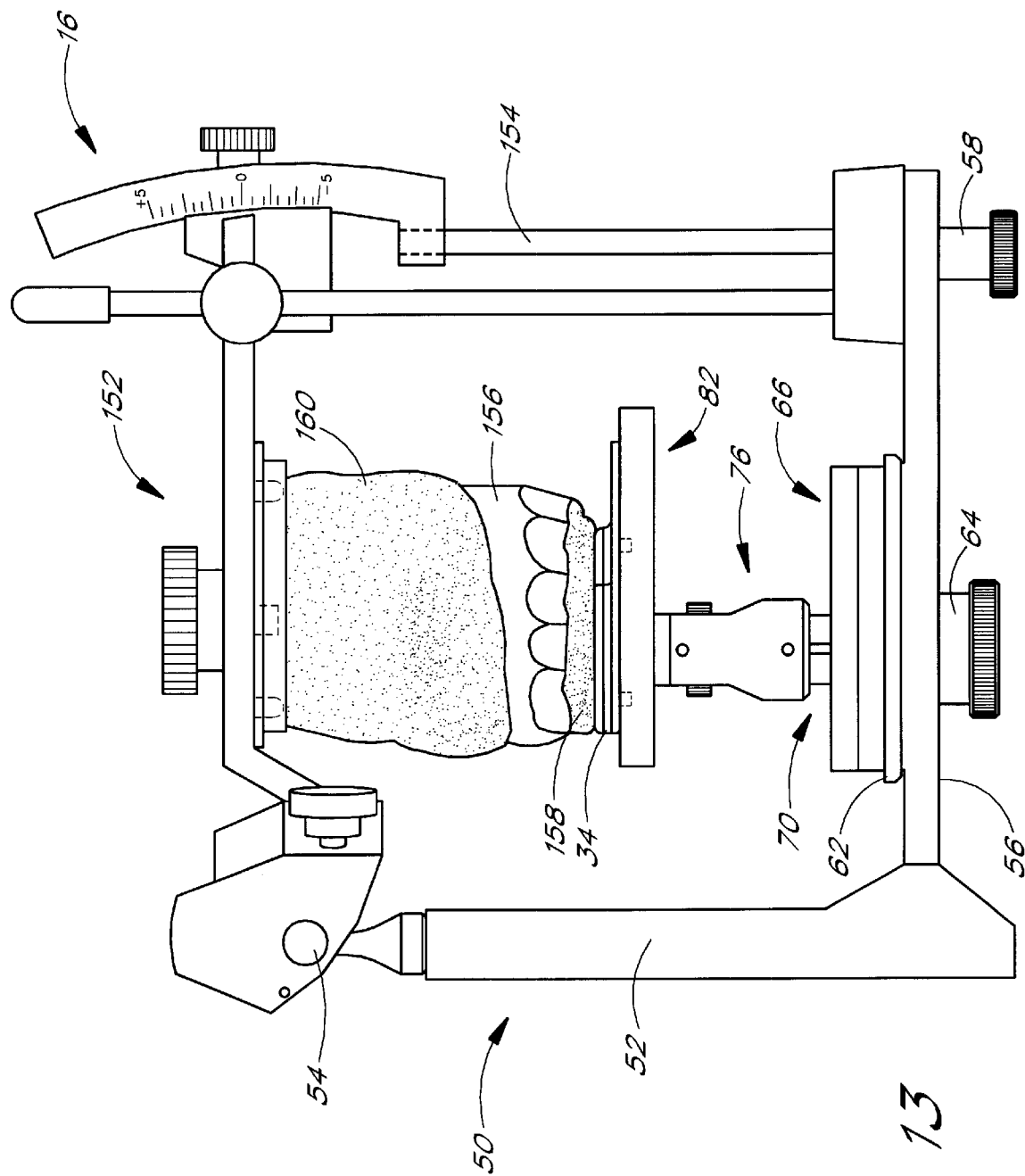
FIG. 13 is a schematic view of an upper dental cast mounted on the index tray in an actuator.

The index tray is now in condition to be used for mounting the patient's maxillary dental cast 156 to the articulator 50. This is accomplished in a known manner. Typically, as seen in FIG. 13, the upper frame 152 of an articulator is positioned on the lower frame 52 axis balls 54 with an incisal pin 154 supporting the forward end of the upper frame being set to zero, which corresponds to a horizontal orientation. The patient's maxillary cast 156 is then positioned on the impressions that are in the bite registration material 158 adhered to the index tray 34, and plaster 160 is utilized to connect the dental cast to the upper frame of the dental articulator.

In shaping the artificial teeth to be formed on the dental cast, the previously recorded information regarding the patient's facial features can be employed to enhance the aesthetic appearance of the prosthetic being formed. For example, the height of the lip commisures can be measured up from the index tray and marked on the dental cast to help evaluate the height of the teeth to enhance the person's smile to the curvature of the lips. Further, the vertical indicator rod can be utilized and analyzed for best considering the length of the incisor or vertical dimension of occlusion in relation to other facial proportions. The mounting platform can be adjusted vertically in millimeters to a desired incisor length. That is, with the dental cast supported by the upper frame of the articulator and the incisal pin, and the platform lowered a desired amount, the length of the incisors could be increased to be aligned with the incisal line on the platform.

What is claimed is:

1. A method of transferring patient dental-facial information to a dental articulator to facilitate the mounting of dental casts on the dental articulator, said method comprising the steps of:

positioning an index tray in a patient's mouth and aligning the facial incisal edge of the patient's maxillary incisors to an incisal line marked on an upper surface of the tray, said tray having soft bite registration material on its upper surface for receiving impressions of the patient's maxillary teeth and registering the patient's plane of occlusion;

instructing the patient to bite lightly into the registration material;

adjusting the tray to a horizontal position with the patient sitting erect and looking straight ahead;

carefully removing the index tray from the patient's mouth after the registration material has set with the tray in said horizontal position; and placing the index tray onto a horizontal mounting platform mounted on the lower frame of a dental articulator, with the mounting platform being centrally positioned from side-to-side and positioned between the upper and lower frames of the articulator, said articulator having supports defining a hinge axis, and said platform being positioned forwardly and downwardly from the hinge axis, the tray being positioned so that the tray incisal line is spaced a known distance from said axis, whereby the index tray is fixed on the mounting platform, in a known relationship corresponding to the patient's specific dental information or average values.

2. The method of claim 1, including the steps of prior to positioning said index tray in the patient's mouth, positioning the tray on a bite fork to support the tray in the patient's mouth, the bite fork being secured to a bow positioned outside of the patient's mouth to facilitate moving the bite fork into the position where it is horizontally aligned.

3. The method of claim 2, wherein said bow includes a centrally located slot positioned forwardly from said plate, and including the steps of positioning a vertical indicator rod in the slot causing the rod to be perpendicular to the bite fork and bow, and sliding the rod close to the patient's face and adjusting the horizontal orientation of said bow to position the rod vertically aligned with the patient's mid-sagittal plane.

4. The method of claim 1, including the steps of prior to positioning said index tray in the patient's mouth, measuring the patient's axis-incisal distance and marking a specific incisal line from an average 100 mm line distance that is marked on the index tray.

5. The method of claim 1, including the step of vertically adjusting the mounting platform in accordance with the patient's dental-facial information or using an average line so that the incisal line on the tray intersects a known vertical line.

6. The method of claim 1, including the steps of
measuring the heights of lip commisures from the index tray; and
sliding markers on a vertical indicator rod to facial landmarks for evaluating facial proportions.

7. Dental apparatus for mounting a dental cast on an articulator in accordance with patient specific dental-facial information or average values, said apparatus comprising:
a face bow analyzer assembly including a face bow having a bite fork, an upper index tray, and a lower index tray, said bite fork being sandwiched between the trays, said trays being adapted to receive dental registration material to provide an impression of a patient's teeth in relation to a patient's face and an average or specific distance from a patients' hinge axis to the patient's maxillary incisal edge, said upper tray having an incisal marking on its upper surface to be aligned with the foremost edges of a patient's maxillary incisors; and
a dental cast mounting platform assembly to be mounted to the lower frame of a dental articulator, the platform assembly including an upper mounting platform configured to mate with said upper tray, said platform having an incisal marking to be aligned with the incisal marking on the upper tray, said platform to be mounted on the articulator at a known distance between a hinge axis on the articulator and the incisal marking on the index tray that is related to the distance between the patient's specific or average hinge axis and the patient's maxillary incisal edge.

8. The apparatus of claim 7, wherein the mounting platform assembly is vertically adjustable and has a measuring scale marked therein.

9. The apparatus of claim 7, wherein the platform assembly is horizontally adjustable and has a measuring scale marked therein.

10. Dental apparatus comprising a face bow comprising a rigid element having a generally flat bite fork configured to be positioned in a patient's mouth between the patient's upper and lower teeth, said bow further having a forward portion connected to the bite fork and being adapted to support a vertical indicator rod in generally perpendicular relation to the bite fork and face bow, and including an upper index tray mounted to said bite fork and configured to receive bite impression material, said upper tray having a marking thereon indicating an incisal line for alignment with the edge of a patient's maxillary incisors.

11. The apparatus of claim 10, wherein said forward portion includes a slot that opens to a front edge of the face bow and extends toward the bite fork, said slot being configured to slidably receive a vertical indicator rod to enable the rod to be slid close to the patient's face when the bite fork is in the patient's mouth.

12. The apparatus of claim 10, wherein said face bow includes a pair of wings extending outwardly from said forward portion to verify horizontal positioning and to facilitate manipulating of the bow by an operator.

13. The apparatus of claim 12, wherein said wings curve rearwardly with respect to the forward portion and are spaced from the bite fork so as to be located adjacent to but spaced from a patient's face when the bite fork is in the patient's mouth.

14. The apparatus of claim 10, wherein said bite fork includes a plurality of holes for receiving pins connected to the upper index tray to maintain correct orientation of the index tray to the bite fork on the face bow.

15. The apparatus of claim 10, including a lower index tray mounted to a bottom surface of said bite fork and being adapted to receive bite impression material to receive a patient's teeth.

16. The apparatus of claim 15, including a plurality of pins depending from said upper tray and extending through holes in said bite fork and into holes in said lower index tray so as to fix the trays to the bite fork.

17. The apparatus of claim 15, including a line formed on the upper surface of said upper tray in a forward portion to be aligned with a patient's incisors when the trays and the bite fork are gripped lightly by the patient's teeth.

18. The apparatus of claim 10, wherein said face bow is a thin flat plate of rigid material.

19. The apparatus of claim 10, including a dental cast mounting assembly including a platform having markings for alignment with said upper tray incisal line.

20. The apparatus of claim 19, wherein said upper index tray and said platform have interengaging pins and holes for securing the tray to the platform.

21. The apparatus of claim 19, wherein said platform markings identify a series of spaced parallel lines representing distances between a patient's hinge axis and a maxillary incisal line.

22. Dental apparatus for mounting a dental cast on an articulator in accordance with patient specific dental-facial information or average values, said apparatus comprising:
an upper index tray adapted to receive dental registration material to provide an impression of a patient's maxillary teeth, said tray having an incisal marking on its upper surface to be aligned with the foremost edges of a patient's maxillary incisors; and
a dental cast mounting platform assembly to be mounted to the lower frame of a dental articulator, the platform assembly including an upper mounting platform configured to mate with said upper tray, so that the incisal marking on the upper tray when mounted on the platform is spaced a known distance from a hinge axis on the articulator and that is related to the distance between the patient's specific or average hinge axis and the patient's maxillary incisal edge.

23. The apparatus of claim 22, wherein the platform has a plurality of incisal markings arranged to be aligned with the marking on the tray, to position the tray markings aligned with a predetermined horizontal distance from said axis.

24. The apparatus of claim 23, wherein the platform and the tray have a plurality of interengaging portions that enable the tray to set the desired hinge axis and incisal line distance.

25. The apparatus of claim 24, wherein said interengaging portions comprise pins on said tray that fit within holes in said platform.

26. The apparatus of claim 25, wherein said platform is vertically adjustable and has a measuring scale in millimeters or inches.

27. The apparatus of claim 25, wherein said platform is horizontally adjustable and has a measuring scale.

28. Dental apparatus comprising a face bow comprising a rigid element having a generally flat bite fork configured to be positioned in a patient's mouth between the patient's upper and lower teeth, said bow further having a forward portion connected to the bite fork and being adapted to support a vertical indicator rod in generally perpendicular relation to the bite fork and face bow, and an upper index tray mounted to an upper surface of said bite fork, and a lower index tray mounted to a bottom surface of said bite fork, said index trays being adapted to receive bite impression material to receive a patient's teeth; and including a plurality of pins depending from said upper tray and extending through holes in said bite fork and into holes in said lower index tray so as to fix the trays to the bite fork.

29. The apparatus of claim 28, wherein said forward portion includes a slot that opens to a front edge of the face bow and extends toward the bite fork, said slot being configured to slidably receive a vertical indicator rod to enable the rod to be slid close to the patient's face when the bite fork is in the patient's mouth.

30. The apparatus of claim 28, wherein said face bow includes a pair of wings extending outwardly from said forward portion to verify horizontal positioning and to facilitate manipulating of the bow by an operator.

31. The apparatus of claim 30, wherein said wings curve rearwardly with respect to the forward portion and are spaced from the bite fork so as to be located adjacent to but spaced from a patient's face when the bite fork is the patient's mouth.

32. The apparatus of claim 28, wherein said face bow is a thin flat plate of rigid material.

33. The apparatus of claim 28, including a dental cast mounting assembly including a platform having markings for alignment with said upper tray incisal line.

34. The apparatus of claim 33, wherein said upper index tray and said platform have interengaging pins and holes for securing the tray to the platform.

35. The apparatus of claim 33, wherein said platform markings identify a series of spaced parallel lines representing distances between a patient's hinge axis and a maxillary incisal line.

36. Dental apparatus comprising a face bow comprising a rigid element having a generally flat bite fork configured to be positioned in a patient's mouth between the patient's upper and lower teeth, said bow further having a forward portion connected to the bite fork and being adapted to support a vertical indicator rod in generally perpendicular relation to the bite fork and face bow, and an upper index tray mounted to an upper surface of said bite fork, and a lower index tray mounted to a bottom surface of said bite fork, said index trays being adapted to receive bite impression material to receive a patient's teeth; and including a line formed on the upper surface of said upper tray in a forward portion to be aligned with a patient's incisors when the trays and the bite fork are gripped lightly by the patient's teeth.

37. The apparatus of claim 36, wherein said forward portion includes a slot that opens to a front edge of the face bow and extends toward the bite fork, said slot being configured to slidably receive a vertical indicator rod to enable the rod to be slid close to the patient's face when the bite fork is in the patient's mouth.

38. The apparatus of claim 36, wherein said face bow includes a pair of wings extending outwardly from said forward portion to verify horizontal positioning and to facilitate manipulating of the bow by an operator.

39. The apparatus of claim 38, wherein said wings curve rearwardly with respect to the forward portion and are spaced from the bite fork so as to be located adjacent to but spaced from a patient's face when the bite fork is in the patient's mouth.

40. The apparatus of claim 36, wherein said face bow is a thin flat plate of rigid material.

41. The apparatus of claim 36, including a dental cast mounting assembly including a platform having markings for alignment with said upper tray incisal line.

42. The apparatus of claim 41, wherein said upper index tray and said platform have interengaging pins and holes for securing the tray to the platform.

43. The apparatus of claim 41, wherein said platform markings identify a series of spaced parallel lines representing distances between a patient's hinge axis and a maxillary incisal line.

44. Dental apparatus comprising a face bow including a thin flat rigid plate having a flat bite fork configured to be positioned in a patient's mouth between the patient's upper and lower teeth and a flat forward portion formed as one piece with the bite fork, said forward portion including a slot that opens to a front edge of the plate and extends toward the bite fork, said slot being configured to slidably receive a vertical indicator rod to enable the rod to be slid close to the patient's face when the bite fork is in the patient's mouth, said plate including a pair of flat wings extending outwardly from and formed as one piece with said forward portion to verify horizontal positioning of the bow and to facilitate manipulating of the bow by an operator, said wings curving rearwardly with respect to the forward portion and being spaced from the bite fork so as to be located adjacent to but spaced from a patient's face when the bite fork is in the patient's mouth.

45. The apparatus of claim 44, wherein said bite fork includes a plurality of holes for receiving pins connected to an upper index tray adapted to be mounted on the bite fork to maintain correct orientation of the index tray to the bite fork on the face bow.

46. The apparatus of claim 44, including an upper index tray mounted to said bite fork and configured to receive bite impression material, said upper tray having an incisal reference for alignment with the edge of a patient's maxillary incisors.

47. The apparatus of claim 46, including a dental cast mounting including a platform having one or more markings for alignment with said upper tray reference.

48. The apparatus of claim 47, wherein said upper index trays and said platform have interengaging pins and holes for securing the tray to the platform.

49. The apparatus of claim 48, wherein said platform markings identify a series of spaced parallel lines representing distances between a patient's hinge axis and a maxillary incisal reference.

50. The apparatus of claim 44, including an upper index tray mounted to an upper surface of said bite fork, and a lower index tray mounted to a bottom surface of said bite fork, said index trays being adapted to receive bite impression material to receive a patient's teeth.

51. The apparatus of claim 50, including a plurality of pins extending from one of said trays and extending through holes in said bite fork and into holes in the other of said trays so as to fix the trays to the bite fork.

52. The apparatus of claim 50, including a reference on said upper tray to be aligned with a patient's incisors when the trays and the bite fork are gripped lightly by the patient's teeth.

53. The apparatus of claim 44, including a holder slidably received in said slot, said holder having an opening for receiving the indicator rod in a vertically adjustable position.

* * * * *

UNITED STATES PATENT AND TRADEMARK OFFICE
CERTIFICATE OF CORRECTION

PATENT NO. : 6,582,931 B1
DATED : June 24, 2003
INVENTOR(S) : Kois et al.

It is certified that error appears in the above-identified patent and that said Letters Patent is hereby corrected as shown below:

Title page,
Item [12], should read -- Lee et al. --
Item [75], Inventors, should read -- Thomas E. Lee, Grand Terrace, CA, John C. Kois, Federal Way, WA (US) --.

Signed and Sealed this

Fourth Day of May, 2004

JON W. DUDAS
*Acting Director of the United States Patent and Trademark Office*